US010096385B1

United States Patent
Thibeault et al.

(10) Patent No.: US 10,096,385 B1
(45) Date of Patent: Oct. 9, 2018

(54) SYSTEM AND METHOD FOR MODEL-BASED ESTIMATION AND CONTROL OF EPIDURAL SPINAL CORD STIMULATION

(71) Applicant: HRL Laboratories, LLC, Malibu, CA (US)

(72) Inventors: Corey M. Thibeault, Encino, CA (US); Narayan Srinivasa, Portland, OR (US)

(73) Assignee: HRL Laboratories, LLC, Malibu, CA (US)

( * ) Notice: Subject to any disclaimer, the term of this patent is extended or adjusted under 35 U.S.C. 154(b) by 28 days.

(21) Appl. No.: 15/219,162

(22) Filed: Jul. 25, 2016

Related U.S. Application Data

(60) Provisional application No. 62/196,238, filed on Jul. 23, 2015.

(51) Int. Cl.
*A61N 1/36* (2006.01)
*G16H 50/50* (2018.01)
*A61N 1/378* (2006.01)
*G06F 19/00* (2018.01)

(52) U.S. Cl.
CPC ......... *G16H 50/50* (2018.01); *A61N 1/36067* (2013.01); *A61N 1/36071* (2013.01); *A61N 1/3787* (2013.01); *G06F 19/3437* (2013.01)

(58) Field of Classification Search
None
See application file for complete search history.

(56) References Cited

U.S. PATENT DOCUMENTS

| | | | | |
|---|---|---|---|---|
| 2005/0222626 A1* | 10/2005 | DiLorenzo | ........... | A61N 1/3605 607/2 |
| 2012/0101326 A1* | 4/2012 | Simon | ................ | A61N 1/36007 600/9 |
| 2014/0257438 A1* | 9/2014 | Simon | .................. | A61N 1/0456 607/72 |
| 2015/0005680 A1* | 1/2015 | Lipani | ................ | A61B 18/1492 601/15 |

(Continued)

OTHER PUBLICATIONS

S. Harkema, V. Gerasimenko, J. Hodes, J. Burdick, C. Angeli, Y. Chen, C. Ferreira, A. Willhite, E. Rejc, R. G. Grossman, et al.,"Effect of epidural stimulation of the lumbosacral spinal cord on voluntary movement, standing, and assisted stepping after motor complete paraplegia: a case study," The Lancet, vol. 377, No. 9781, pp. 1938-1947, 2011.

(Continued)

*Primary Examiner* — Kennedy Schaetzle
(74) *Attorney, Agent, or Firm* — Tope-McKay & Associates

(57) ABSTRACT

Described is a system for controlling epidural spinal cord stimulation. Using an Unscented Kalman Filter (UKF), the system receives sensed physiological signals from a subject and, based on the sensed physiological signals, estimating an unobservable state of a target area on the subject. A central pattern generator is then used to generate a stimulation pattern based on the unobservable state. The stimulation pattern is applied to the target area (e.g., spinal cord) of the subject using an electrode array. Receiving feedback, the UKF continuously updates a model of the spinal cord, which results in adjustment of the stimulation pattern as necessary.

24 Claims, 5 Drawing Sheets

(56) References Cited

U.S. PATENT DOCUMENTS

2016/0175586 A1\* 6/2016 Edgerton .......... A61N 1/36003 604/20

OTHER PUBLICATIONS

I. A. Rybak, N. A. Shevtsova, M. Lafreniere-Roula, and D. A. McCrea, "Modelling spinal circuitry involved in locomotor pattern generation: insights from deletions during fictive locomotion," The Journal of physiology, vol. 577, No. 2, pp. 617-639, 2006.

D. A. McCrea and I. A. Rybak, "Modeling the mammalian locomotor cpg: insights from mistakes and perturbations," Progress in brain research, vol. 165, pp. 235-253, 2007.

S. J. Schiff and T. Sauer, "Kalman filter control of a model of spatiotemporal cortical dynamics," BMC Neuroscience, vol. 9, No. Suppl 1, pp. 1-2, 2008.

G. Ullah and S. J. Schiff, "Assimilating seizure dynamics," PLoS Comput Biol, vol. 6, pp. e1000776-1-e1000776-12, May 2010.

G. Ullah and S. J. Schiff, "Tracking and control of neuronal hodgkin-huxley dynamics," Phys. Rev. E, vol. 79, pp. 040901-1-040901-4, Apr. 2009.

S. J. Schiff, "Towards model-based control of parkinson's disease," Philosophical Transactions of the Royal Society A: Mathematical, Physical and Engineering Sciences, vol. 368, No. 1918, pp. 2269-2308, 2010.

S. J. Schiff, Neural Control Engineering the Emerging Intersection between Control Theory and Neuroscience, The MIT Press, 2012. Chapter on "Control Systems with Electrical Fields," pp. 273-301.

H. U. Voss, J. Timmer, and J. Kurths, "Nonlinear dynamical system identification from uncertain and indirect measurements.," I. J. Bifurcation and Chaos, pp. 1905-1933, 2004.

H. D. I. Abarbanel, D. R. Creveling, and J. M. Jeanne, "Estimation of parameters in nonlinear systems using balanced synchronization," Phys. Rev. E, vol. 77, pp. 016208-1-016208-14, Jan. 2008.

J. Aprasoff and O. Donchin, "Correlations in state space can cause sub-optimal adaptation of optimal feedback control models," Journal of Computational Neuroscience, vol. 32, pp. 297-307, 2012.

X.-J. Feng, E. Shea-Brown, B. Greenwald, R. Kosut, and H. Rabitz, "Optimal deep brain stimulation of the subthalamic nucleusa computational study," Journal of Computational Neuroscience, vol. 23, pp. 265-282, 2007.

J. Rubin and D. Terman, "High frequency stimulation of the subthalamic nucleus eliminates pathological thalamic rhythmicity in a computational model," Journal of Computational Neuroscience, vol. 16, No. 3, pp. 211-235, 2004.

J. Modolo, A. Legros, A. W. Thomas, and A. Beuter, "Model-driven therapeutic treatment of neurological disorders: reshaping brain rhythms with neuromodulation," Interface Focus, vol. 1, No. 1, pp. 61-74, 2011.

R. van den Brand, J. Heutschi, Q. Barraud, J. DiGiovanna, K. Bartholdi, M. Huerlimann, L. Friedli, I. Vollenweider, E. M. Moraud, S. Duis, et al., "Restoring voluntary control of locomotion after paralyzing spinal cord injury," Science, vol. 336, No. 6085, pp. 1182-1185, 2012.

Beekhuizen KS, Field-Fote EC, "Massed practice versus massed practice with stimulaton: Effects on upper extremity function and cortical plasticity in individuals with incomplete cervical spinal cord injury," Neurorehabil Neural Repair. 2005;19(1): pp. 33-45.

Molkov, Y., Zoccal, D., Moraes, D., Paton, J., Machado, B. and Rybak, I. 2011, "Intermittent hypoxia-induced sensitization of central chemoreceptors contributes to sympathetic nerve activity during late expiration in rats," J Neurophysiol 105: pp. 3080-3091. Doi:10.1152/jn.00070.2011.

Shigeru Kuriyama, Yoshimi Kurihara, Yusuke Irino, and Toyohisa Kaneko, "Physiological Gaits Controls with a Neural Pattern Generator", The Journal of Visualization and Computer Animation, vol. 13, No. 2, pp. 107-119, 2002.

Little JW, Micklesen P, Umlaut R, Britell C., "Lower extremity manifestations of spasticity in chronic spinal cord injury," Am J Phys Med Rehabil 1989;68: pp. 32-36.

Thibeault Corey Michael, "A role for neuromorphic processors in therapeutic nervous system stimulation", Frontiers in Systems Neuroscience, vol. 8, pp. 1-3, 2014, No. 00187.

\* cited by examiner

SYSTEM AND METHOD FOR MODEL-BASED ESTIMATION AND CONTROL OF EPIDURAL SPINAL CORD STIMULATION

GOVERNMENT RIGHTS

This invention was made with government support under U.S. Government Contract Number HR0011-09-C-0001. The government has certain rights in the invention.

CROSS-REFERENCE TO RELATED APPLICATIONS

This is a non-provisional patent application of 62/196,238, filed on Jul. 23, 2015, the entirety of which is hereby incorporated by reference.

BACKGROUND OF INVENTION

(1) Field of Invention

The present invention relates to a neural stimulation system and, more specifically, to a system for model-based estimation and control of epidural spinal cord stimulation.

(2) Description of Related Art

The recent discoveries in the use of electrical stimulation on patients with motor complete paraplegia has revealed a therapeutic pathway towards restoring voluntary motor function (see the List of Incorporated Literature References, Literature Reference No. 9). However, the mechanisms behind this benefit as well as the supporting technology is severely lacking. The current state-of-the-art involves randomly tuning the stimulation parameters manually until a physiological improvement is observed—these parameters include both the duration and amplitude of the stimulus as well as anode/cathode pairings.

In other prior art, the patent described by Dilorenzo et al. in Literature Reference No. 1 consists of a method and apparatus for feedback control of stimulation to the nervous system. It describes the use of an "adaptive model of disease behavior to estimate disease states which are not directly detectable from sensors", but does not deal with spinal cord injury or neuromorphic processors.

The patent of Bradley et al. in Literature Reference No. 2 describes a method for efficiently searching for an effective spinal cord stimulation system parameter sets. It involves selecting a set of stimulation output values and iterating over those to find the highest therapeutic benefit. The method only describes the creation of a parameter space that can be tested, and relies upon exhaustive testing of stimulation outputs in a laboratory setting that is time and resource intensive. There is no modeling of the area under stimulation as a solution to the optimization problem and feedback has to be provided by the patient. Further, neuroplastic phenomena and the subsequent remodeling of circuits following injury change the underlying physical system for motor control. This represents a constantly shifting stimulation parameter space (see Literature Reference No. 24) that necessitates frequent updates of established stimulation protocol that is unaccounted for using the above method.

The patent for Rise in Literature Reference No. 3 describes a system that monitors the cardiac signals of a patient as part of a feedback controller for stimulating the spinal cord in the treatment of angina. This does not address model-based control, rehabilitation from spinal cord injury, or neuromorphic hardware.

The patent for Libbus et al. in Literature Reference No. 4 describes a closed loop stimulation system targeting the autonomic nervous system. It claims to target devices and methods for sensing nerve traffic and providing closed-loop neural stimulation based on sensed nerve traffic. It does not describe using a model-based system for that control interface or the use of neuromorphic hardware.

The patent of Libbus et al. in Literature Reference No. 5 describes a feedback control system that monitors the motion of a patient and detects unintended movement to tune the stimulus provided to parts of the autonomic nervous system. It does not describe a model-based system the use of neuromorphic hardware.

In other prior art, the patent for King et al. in Literature Reference No. 6 describes a closed loop system for stimulating the spinal cord (among other areas) based on the feedback provided by a sensor measuring a patient's blood flow. It does not describe using a model-based system for that control interface or the use of neuromorphic hardware.

The patent described by Hoffer et al. in Literature Reference No. 7 comprises a system for the partial restoration of motor functions. The closed-loop system uses force sensors to provide feedback to a control directly stimulating muscles. The control is described as a combination of proportional, integral or derivative feedback but does not describe model based control. It does not describe stimulating the spinal cord or the use of neuromorphic hardware.

Further, the patent by Whitehurst et al. in Literature Reference No. 8 describes a spinal cord stimulator for the treatment of pain. The device is not closed loop and does not discuss recovery from spinal cord injury or neuromorphic hardware.

Although there are existing spinal cord stimulation technologies, there are none that employ a model-based feedback control strategy or that describe such a strategy using neuromorphic hardware. Thus, a continuing need exists for a system for model-based estimation, control, and updating of parameters for epidural spinal cord stimulation.

SUMMARY OF INVENTION

This disclosure provides a system for controlling epidural spinal cord stimulation. In various embodiments, the system comprises one or more processors and a memory, the memory being a non-transitory computer-readable medium having executable instructions encoded thereon, such that upon execution of the instructions, the one or more processors perform several operations, including receiving sensed physiological signals from a subject and, based on the sensed physiological signals, estimating an unobservable state of a target area on the subject; and generating a stimulation pattern based on the unobservable state for applying to the target area on the subject using an electrode array.

In other aspect, the stimulation pattern is generated using a central pattern generator.

Further, in estimating the unobservable state of the target area of the subject, an Unscented Kalman Filter (UKF) is used that employs a set of known dynamical equations and observation functions with observable data to update an approximation of the unobservable state.

Additionally, the stimulation pattern is simultaneously applied to the target area of the subject and into a model of spinal cord state as defined by a Function F of the UKF.

In yet other aspects, the UKF updates the model of the spinal cord based on predicted motor responses and the physiological signals, with the stimulation pattern modified based on the updates model of the spinal cord.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
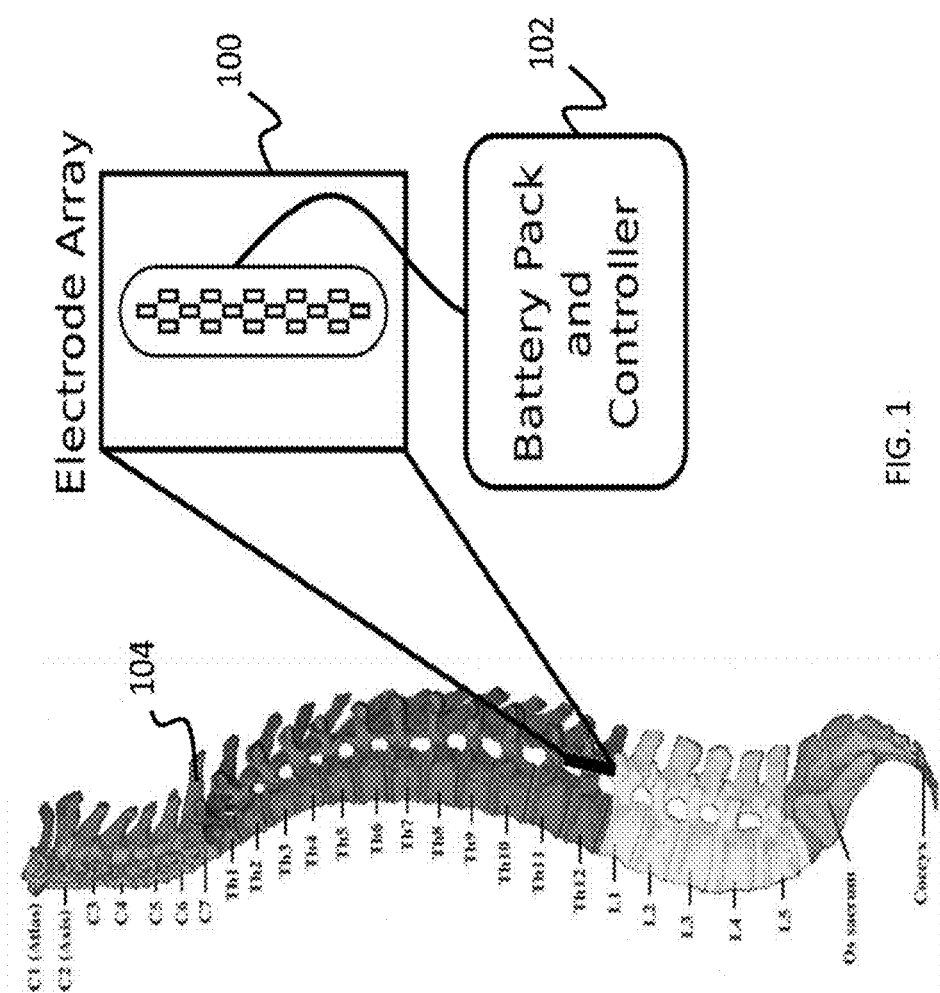
FIG. 1 is an illustration depicting an example placement of an electrode stimulation array.

The present invention relates to a neural stimulation system and, more specifically, to a system for model-based estimation and control of epidural spinal cord stimulation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) LIST OF INCORPORATED LITERATURE REFERENCES

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. D. DiLorenzo, "Apparatus and method for closed-loop intracranical stimulation for optimal control of neurological disease," Apr. 2, 2002. U.S. Pat. No. 6,366,813.
2. K. Bradley, J. Thacker, C. Woods, and J. King, "Method for optimizing search for spinal cord stimulation parameter setting," Nov. 22, 2011. U.S. Pat. No. 8,065,013.
3. M. Rise, "Method and apparatus for providing feedback to spinal cord stimulation for angina," October 1998. U.S. Pat. No. 5,824,021.
4. I. Libbus, A. Kramer, and J. Moffitt, "System and method for closed-loop neural stimulation," March 2013. U.S. Pat. No. 8,396,560.
5. I. Libbus and A. Kramer, "Automatic neural stimulation modulation based on motion and physiological activity," Oct. 9, 2012. U.S. Pat. No. 8,285,389.
6. G. King, "Apparatus and method for treating peripheral vascular disease and organ ischemia by electrical stimulation with closed loop feedback control," May 2, 2000. U.S. Pat. No. 6,058,331.
7. J. Hoffer, "Closed-loop, implanted-sensor, functional electrical stimulation system for partial restoration of motor functions," Jun. 14, 1988. U.S. Pat. No. 4,750,499.
8. T. Whitehurst, J. McGivern, C. Mann, and J. Kuzma, "Fully implantable microstimulator for spinal cord stimulation as a therapy for chronic pain," Mar. 22, 2005. U.S. Pat. No. 6,871,099.
9. S. Harkema, Y. Gerasimenko, J. Hodes, J. Burdick, C. Angeli, Y. Chen, C. Ferreira, A. Willhite, E. Rejc, R. G. Grossman, et al., "Effect of epidural stimulation of the lumbosacral spinal cord on voluntary movement, standing, and assisted stepping after motor complete paraplegia: a case study," The Lancet, vol. 377, no. 9781, pp. 1938-1947, 2011.
10. I. A. Rybak, N. A. Shevtsova, M. Lafreniere-Roula, and D. A. McCrea, "Modelling spinal circuitry involved in locomotor pattern generation: insights from deletions during fictive locomotion," The Journal of physiology, vol. 577, no. 2, pp. 617-639, 2006.

11. D. A. McCrea and I. A. Rybak, "Modeling the mammalian locomotor cpg: insights from mistakes and perturbations," Progress in brain research, vol. 165, pp. 235-253, 2007.
12. S. J. Schiff and T. Sauer, "Kalman filter control of a model of spatiotemporal cortical dynamics," BMC Neuroscience, vol. 9, no. Suppl 1, p. O1, 2008.
13. G. Ullah and S. J. Schiff, "Assimilating seizure dynamics," PLoS Comput Biol, vol. 6, p. e1000776, 05 2010.
14. G. Ullah and S. J. Schiff, "Tracking and control of neuronal hodgkin-huxley dynamics," Phys. Rev. E, vol. 79, p. 040901, April 2009.
15. S. J. Schiff, "Towards model-based control of parkinson's disease," Philosophical Transactions of the Royal Society A: Mathematical, Physical and Engineering Sciences, vol. 368, no. 1918, pp. 2269-2308, 2010.
16. S. J. Schiff, Neural Control Engineering The Emerging Intersection between Control Theory and Neuroscience. The MIT Press, 2012.
17. H. U. Voss, J. Timmer, and J. Kurths, "Nonlinear dynamical system identification from uncertain and indirect measurements," I. J. Bifurcation and Chaos, pp. 1905-1933, 2004.
18. H. D. I. Abarbanel, D. R. Creveling, and J. M. Jeanne, "Estimation of parameters in nonlinear systems using balanced synchronization," Phys. Rev. E, vol. 77, p. 016208, January 2008.
19. J. Aprasoff and O. Donchin, "Correlations in state space can cause suboptimal adaptation of optimal feedback control models," Journal of Computational Neuroscience, vol. 32, pp. 297-307, 2012.
20. X.-J. Feng, E. Shea-Brown, B. Greenwald, R. Kosut, and H. Rabitz, "Optimal deep brain stimulation of the subthalamic nucleusa computational study," Journal of Computational Neuroscience, vol. 23, pp. 265-282, 2007.
21. J. Rubin and D. Terman, "High frequency stimulation of the subthalamic nucleus eliminates pathological thalamic rhythmicity in a computational model," Journal of Computational Neuroscience, vol. 16, no. 3, pp. 211-235, 2004.
22. J. Modolo, A. Legros, A. W. Thomas, and A. Beuter, "Model-driven therapeutic treatment of neurological disorders: reshaping brain rhythms with neuromodulation," Interface Focus, vol. 1, no. 1, pp. 61-74, 2011.
23. R. van den Brand, J. Heutschi, Q. Barraud, J. DiGiovanna, K. Bartholdi, M. Huerlimann, L. Friedli, I. Vollenweider, E. M. Moraud, S. Duis, et al., "Restoring voluntary control of locomotion after paralyzing spinal cord injury," Science, vol. 336, no. 6085, pp. 1182-1185, 2012.
24. Beekhuizen K S, Field-Fote EC, "Massed practice versus massed practice with stimulation: Effects on upper extremity function and cortical plasticity in individuals with incomplete cervical spinal cord injury," Neurorehabil Neural Repair. 2005; 19(1):33-45.
25. Molkov, Y., Zoccal, D., Moraes, D., Paton, J., Machado, B. and Rybak, I. 2011, "Intermittent hypoxia-induced sensitization of central chemoreceptors contributes to sympathetic nerve activity during late expiration in rats," J Neurophysiol 105: pp. 3080-3091. Doi: 10.1152/jn.00070.2011.
26. Shigeru Kuriyama, Yoshimi Kurihara, Yusuke Irino, and Toyohisa Kaneko, "Physiological Gaits Controls with a Neural Pattern Generator", The Journal of Visualization and Computer Animation, Vol. 13, No. 2, pp. 107-119, 2002.
27. Little J W, Micklesen P, Umlauf R, Britell C., "Lower extremity manifestations of spasticity in chronic spinal cord injury," Am J Phys Med Rehabil 1989; 68:32-6.
28. Thibeault Corey Michael, "A role for neuromorphic processors in therapeutic nervous system stimulation", Frontiers in Systems Neuroscience, Vol. 8, 2014, No. 00187.

(2) PRINCIPAL ASPECTS

Various embodiments of the invention include two "principal" aspects. The first is a system for model-based estimation and control of epidural spinal cord stimulation. The system is typically in the form of a system operating software or in the form of a hard-coded instruction set and can include various neural hardware, sensors, and stimulators (e.g., electrodes) as described herein to perform the various features and functions as described. This system may be incorporated into a wide variety of devices that provide different functionalities. The second principal aspect is a method, typically in the form of software or instructions or processes performed by the neural hardware, sensors and/or stimulators as described herein. These aspects will be described in more detail below.

(3) INTRODUCTION

This disclosure provides a system and method for model-based estimation and control of epidural spinal cord stimulation. The system improves the efficacy of spinal cord stimulation in restoring voluntary movement of people with motor complete paraplegia using neuromorphic hardware and two different model based strategies. The system performs state estimation employing a model based observer system to assist in, or automate, the stimulation protocol parameter selection. Efficient feedback control of a stimulator is provided using a model based controller strategy. By using the model based control strategy, the physiological state of the area under stimulation can be estimated and used to find a therapeutic benefit. This same estimation strategy can then be used to dynamically alter the stimulation protocol after implantation, thereby providing a mechanism of maintaining, or even improving, the benefit, as well as adjusting for physiological changes in the underlying system common to many types of spinal cord injury.

Currently all implantable neural stimulation devices are open loop control and a constant stimulus is applied. In the case of spinal cord stimulation that constant input is randomly changed by researchers until a physiological improvement is observed. Not only does this not guarantee that these parameters lie in a local minimum of a cost function but there is also no limit to how long it takes to find a parameter set with a therapeutic benefit. Testing in this manner also requires expert personnel in a laboratory setting; dynamic changes in physiology necessitate frequent adjustments of stimulation parameters which may not be feasible given the limited accessibility of facilities and staff.

This disclosure fills a gap in the technology and is capable of observing and controlling spinal circuits during epidural stimulation. A first embodiment of this concept involves an automated implementation for converging on a set of optimal parameters, while a second embodiment builds on the first by adding a feedback control system. Both of these embodiments can be further extended into efficient low-power neuromorphic circuits. Without this advancement the power consumption of this system would likely be too high for use in an implantable device, which often rely on battery power and rely on frequent recharge cycles. As can be appreciated by those skilled in the art, this disclosure provides a huge breakthrough in medical device design. Specific details are provided below.

(4) SPECIFIC DETAILS OF VARIOUS EMBODIMENTS

As noted above, recent discoveries in the use of electrical stimulation on patients with motor complete paraplegia has revealed a therapeutic pathway towards restoring voluntary motor function. The current state-of-the-art involves randomly tuning the stimulation parameters manually until a physiological improvement is observed—these parameters include both the duration and amplitude of the stimulus as well as anode/cathode pairings. The system and method of this disclosure revolutionizes that process by not only automating the parameter selection but by dynamically changing it throughout the lifetime of the implant. This can be accomplished by combining model based control strategies with power efficient neuromorphic hardware.

By using a model of the area under stimulation, both the activity and state of that area can be approximated (something that is not directly measurable). The model, constructed from the current understanding of the anatomy, can then be used to find an optimal set of stimulation parameters. In addition, the model output can be used as the feedback into a control system that can not only dynamically tune the stimulation parameters but also adapt to the physiological circuit remodeling, thereby providing the highest possible therapeutic benefit.

By embedding these models in low-power neuromorphic hardware (such as those developed in the DARPA SyNAPSE program), this model-based control strategy is feasible in implantable devices. The DARPA SyNAPSE program is a government funded program that that is directed to developing electronic neuromorphic machine technology that scales to biological levels. The Defense Advanced Research Project Agency (DARPA) is located at 675 North Randolph Street, Arlington, Va. 22203-2114. Thus, described herein is a system that can provide the estimation and control of the mammalian spinal cord after injury under epidural stimulation using low-power neuromorphic hardware. A process of using neuromorphic processors in therapeutic nervous system stimulation was also described by the inventor in Literature Reference No. 28. Further details regarding the system are described below.

(4.1) Epidural Spinal Cord Stimulation

Epidural spinal cord stimulation was first approved for use in pain therapy. However, the work of Harkema et al. (see Literature Reference No. 9) demonstrated that it is possible to reactivate the neural pathways responsible for motor control even after clinically complete paraplegia. In these experiments and as shown in FIG. 1, a stimulator (i.e., electrode array 100) and a controller and battery pack 102 were implanted in the patient 104. Thus and as understood by those skilled in the art, the electrode array 100 is operable for stimulating the neurons and reactivating neural pathways. Such an electrode array 100 can be incorporated into the system according to various embodiments of the present invention. Note that although a 16 electrode array is depicted as being positioned and attached at a particular spinal location, the present invention is not intended to be limited thereto as any suitable number of electrodes and locations can be implemented as needed per the particular patient and application.

(4.2) Model Based Predictors

Model based or model predictor control systems work as state estimators where the dynamics of the model are used to predict (estimate) the state of the current system. That prediction is then corrected with new measurements. These allows us to incorporate the predictions of the system's state as well as sensor estimates with the real sensor information to get a better estimate of the actual state. Specific details regarding the model based approach of the present invention is provided below.

(4.3) Central Pattern Generators

Figure 2:
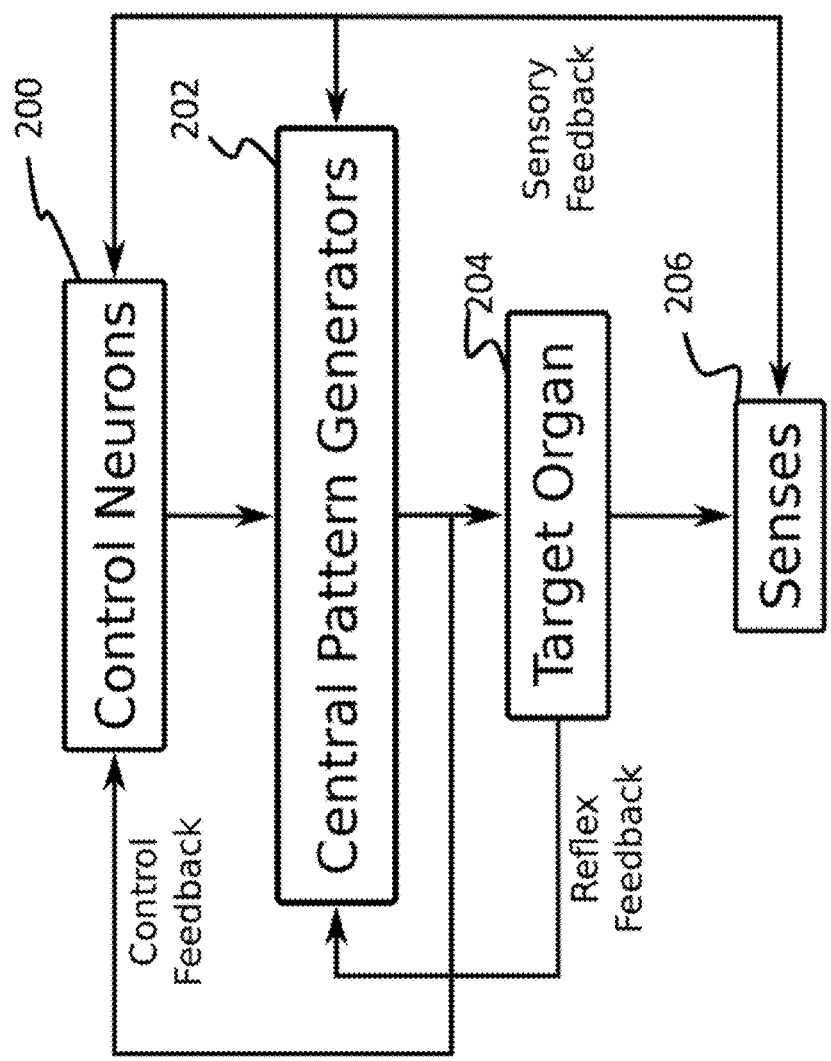
FIG. 2 is a flowchart depicting motor control hierarchy of a system according to various embodiments of the present invention.

The mammalian spinal cord relies on central pattern generators (CPG) to generate locomotive motor output to the body. Although CPGs can produce the requisite rhythmic activity in the absence of both sensory feedback and higher-level innervation, both are required to effectively shape and control the output of the CPG. These are all components of the motor control hierarchy outline as shown in FIG. 2. As shown, control neurons 200 provide basic command outputs to the CPG 202. The target organ 204, such as the downstream muscle targets of stimulation, provide reflexive feedback to the CPG 202. The reflexive feedback is, for example, the force demands placed upon tendon stretch organs and proprioceptive information from the joint angle sensors that describe and update the state of motor anatomy. Additional sensory information, such as that from touch receptors and pressure-sensitive corpuscles provide CPG 202 and higher processing neurons 200 with additional feedback. Based on the command output from the control neurons, the reflexive feedback, and the sensory feedback, the CPG 202 generates a dynamic stimulation pattern to the target organ 204 that enables normal motor function.

It should be understood that any suitable CPG model can be used to implement the process and system as described herein. For example, there are a number of CPG models compatible with the SyNAPSE neuromorphic hardware design (see, for example, Literature Reference Nos. 10 and 11). Other examples of CPG models include those found and illustrated in Literature Reference Nos. 25 and 26.

(4.4) Observer System and State Estimation with Neuromorphic Hardware

It is desirable to monitor neural circuits and observe system variables. One strategy for estimating these unknown system variables and parameters is by employing an Unscented Kalman Filter (UKF) to combine the observable and unobservable states. The UKF employs a set of known dynamical equations and observation functions with the observable data to update an approximation of the state and its uncertainty. At each update, sigma points (i.e., system states that are consistent with the current state uncertainty) are selected and used to integrate the system. These are combined with estimated mean state values and the approximate uncertainty. The Kalman gain matrix then updates the new most likely state of the system.

The UKF can be generally described by the following. The system dynamics are described by a function, F, and the observations are described by a function, A. In most systems those observations are going to be noisy, so a covariance matrix, R, will account for that.

For a D-dimensional estimated state, $\bar{x}$, the two-dimensional sigma points, $X_i$, are the combination of the D columns of the matrices $\bar{x}+\sqrt{DP}$ and $\bar{x}-\sqrt{DP}$. Where P is the estimated covariance matrix and the matrix square root is taken. After one step of F, using the resulting sigma points will provide $\tilde{X}_i=F(X_i)$. A new set of observations can then be found, $\tilde{Y}_i=A(X_i)$. The means over these two matrices are the a priori state and measurement estimates. These are then used to calculate the ensemble a priori covariances, $\tilde{P}_{XX}$, $\tilde{P}_{XY}$, and $\tilde{P}_{YY}$. The a posteriori state estimate, $\hat{x}$, is now dependent on the state estimate, $\tilde{x}$, the measurement estimate, $\tilde{y}$, the actual measurement, y, and the Kalman gain matrix. Similarly, the a posteriori, $\hat{P}_{XX}$, can be calculated using the a priori covariances and the Kalman gain matrix. The schematic for this organization is illustrated in FIG. 3.

Figure 3:
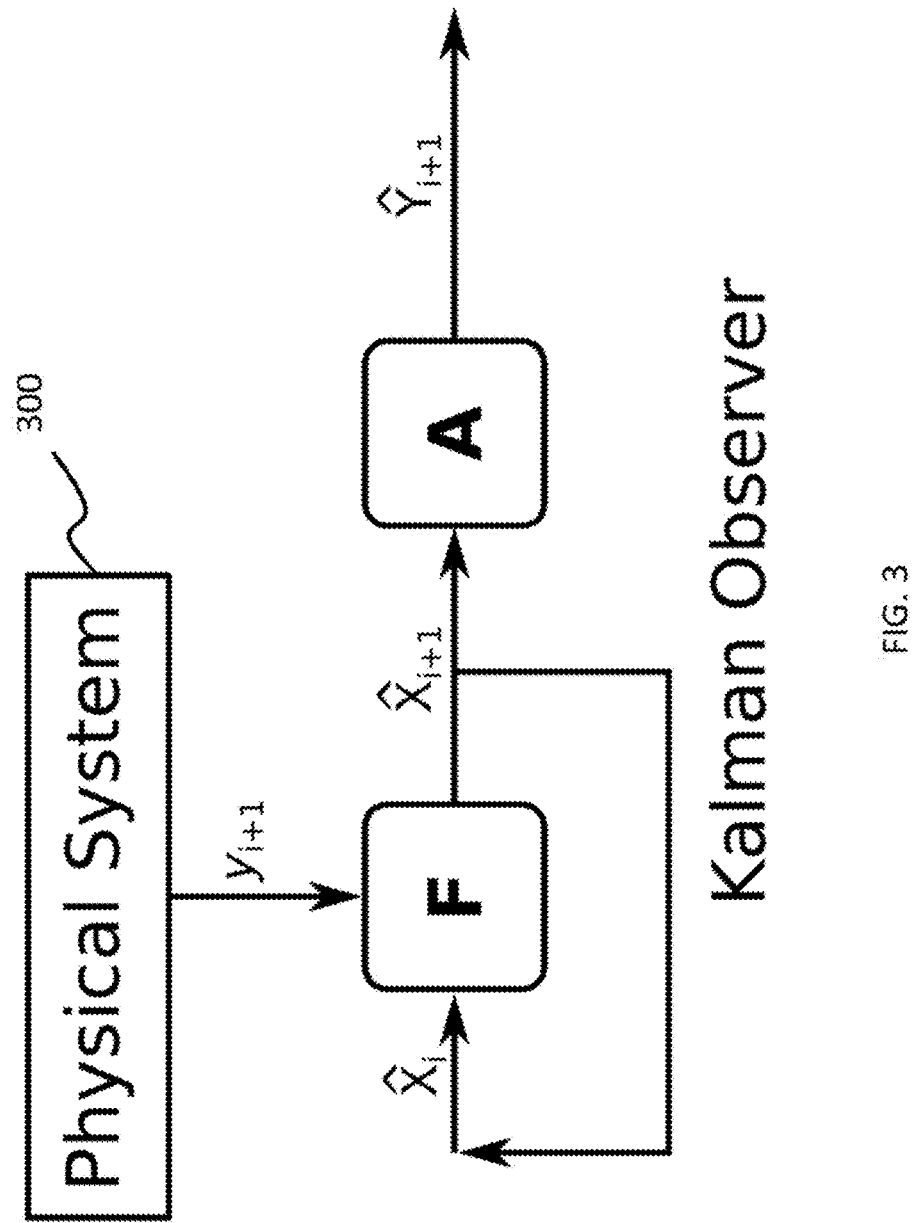
FIG. 3 is flowchart depicting a simplified Kalman observer according to various embodiments of the present invention.

As shown in FIG. 3, the physical system 300 represents the interface between stimulation system and spinal cord to be optimized by Function F. Function F computes a model of physical system, allowing the selection and input of optimized stimulation parameters that maximize some desired behavior from physical system 300. The output of Function F is fed back into the function and also on to Function A, which represents the outputs provided by the model of the physical system F. Based on the feedback information, the accuracy of function F can be determined by comparing the outputs of the real physical system 300, and the outputs observed through function A. Examples of applying this to a neural system can be found in Literature Reference Nos. 12 through 16.

In the paradigm provided by this disclosure, the dynamic function F is calculated using a model of the biological circuits. When the neuron population is large and biological fidelity is required, the coupled differential equations used to model these neurons can take significant computational resources. This is where the low-power neuromorphic hardware would be applied. Without this low-power solution, an implantable system that could provide both a therapeutic benefit and long battery life would be difficult if not infeasible.

This aspect of the invention tracks the state of an observed simulated neural model (e.g., spinal cord model) and estimates the unobservable parameters of that model (i.e., spinal cord model). The Unscented Kalman Filter (UKF) is a generalized modelling technique that assumes that unobservable elements/parameters of a given physical system exist and affect the behavior of that system, but attempts to account for/model these parameters even if they are not measurable. Thus, function F is an encapsulation of the biological circuitry, a set of equations designed to replicate the behavior of the physical system 300 mathematically. UKF is a step that allows updates and improvements to the model (e.g., spinal cord model) over time (it is available as a freely available technique/software package) that links the physical system 300 with the dynamic function F in order to update/improve the model's accuracy over time. Neuromorphic hardware is incorporated within the system to consume small amounts of energy suitable for ultra-portable/ultra-low power applications while still performing the necessary computations to enable this device.

The ability to obtain (i.e., estimate) these unobservable quantities provides the necessary technology for automatically searching for the most appropriate stimulation parameters during therapy. In addition, it provides the foundation for developing feedback control systems that can fully adapt to the system.

(4.5) Model-Based Controller

The observability of a system does not guarantee its controllability but, it is a necessary requirement. Using the outcomes of the State Estimation as set forth above in Section 4.4, a feedback control system for epidural stimulation can be added. The use of model based control strategies for neural circuits not only provides a therapeutic advantage to existing technologies but can also result in lower power consumption, leading to longer battery life and fewer invasive surgeries to replace them.

Figure 4:
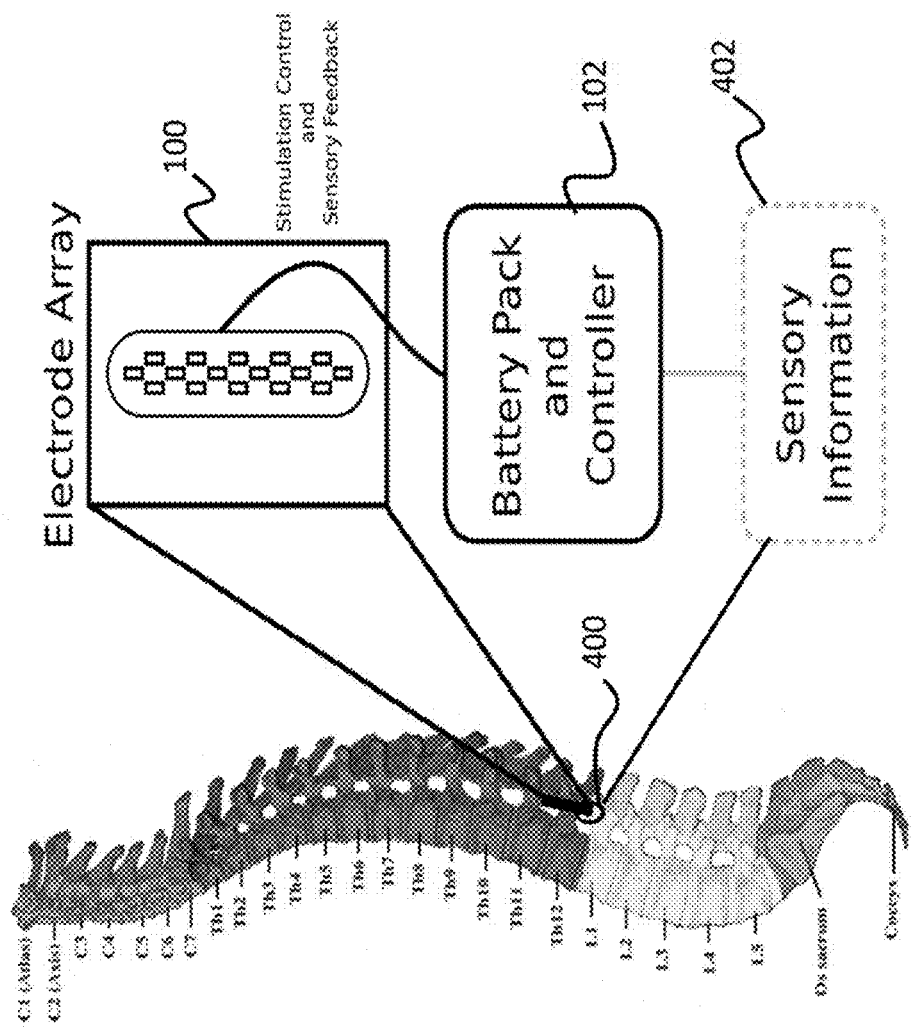
FIG. 4 is an illustration depicting motor control and a feedback into the controller according to various embodiments of the present invention.

The feedback to the controller can come from a number of different places. FIG. 4, for example, illustrates that feedback into the controller 102 can come from external sources or from electrodes 100 themselves in between pules. In between pulses the stimulator electrodes 100 could be used to monitor the local field potentials of the CPG circuits. Alternatively, separate sensors 400 could be implanted to provide neural and muscular sensory information 402 feedback to the controller 102.

The work of Voss et al. (see Literature Reference No. 17) demonstrated one of the first examples of combining dynamical control theory and electrophysiology where the state of a reduced neuron model was estimated using an unscented Kalman filter. This helped establish the strategies for observing and controlling the highly non-linear dynamics of neural systems. Although that original application contained only a single neuron and merely estimated the missing model parameters, subsequent work has demonstrated the strategy in additional control and estimation paradigms (see, for example, Literature Reference Nos. 13 through 16, 18, and 19).

Figure 5:
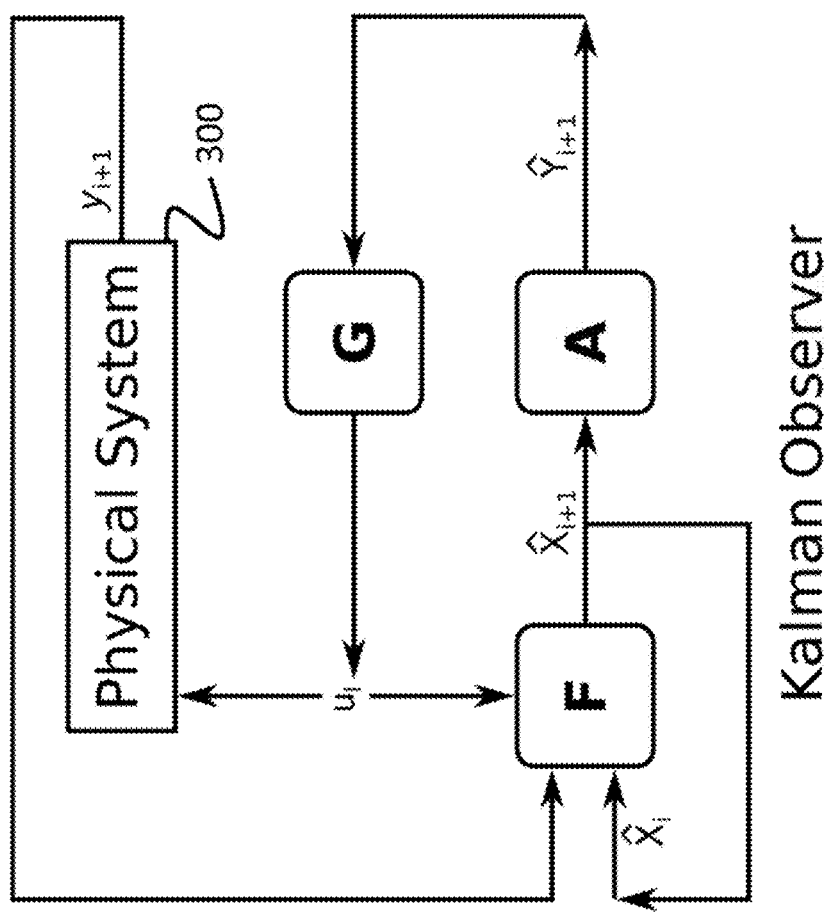
FIG. 5 is a flowchart depicting a closed loop system according to various embodiments of the present invention.

An example of the feedback control (i.e., as incorporated into the controller 102 of FIG. 4) is illustrated in FIG. 5. This is a simplified schematic as only a gain function, G, for generating the control signal is added, but it illustrates how the state output of the observer system can be used to create a control signal for the stimulation in the physical system 300. See, for example, Literature Reference Nos. 12 through 16 for example implementations of using a feedback paradigm for brain implants.

As can be appreciated by those skilled in the art, there are a number of ways a cost function for the stimulation could be incorporated. For example, in Feng et al. (see Literature Reference No. 20), a spike transfer reliability function (see Literature Reference No. 21) was combined with a correlation measure. Something similar can be used in this instance where the reliability of spikes being relayed across or around the damaged circuit to the target limb can be coupled with estimates of the synchronization of the spinal circuits. Removing unwanted oscillations has been another strategy in feedback control systems (see Literature Reference No. 22). In addition to these, the frequency of the central pattern-generator may be an appropriate measure for altering the control signal and balancing the power with the therapeutic benefit. As a non-limiting example, the physiology of the post-injury spinal cord may converge on a specific endogenous frequency for maximal therapeutic benefit. The system, detecting suboptimal motor outputs upon applying stimulation, will update the model to compensate for these changes and the stimulation parameters will be changed to the new, maximally effective operating frequency. In another non-limiting instance, damaged tracts in the spinal cord anatomy may exhibit aberrant behavior, such as spasticity (see Literature Reference No. 27), likely resulting from dying cells in the CPG and sensory systems. In these cases, the dynamic equations computing the state of the system can be written in such a way that the goal state of the system converges towards suppression of oscillations belonging to frequency bands located outside the operating frequency of the CPG. Rather than eliciting motor activity in this case, the system would dynamically apply stimulation to alleviate activity such as spasms, ballismus, and clonus.

Model based control concepts have a number of clinical and practical applications (see, for example, Literature Reference No. 16). However, they can be computationally expensive. In addition to the control system computations, are the numerical calculations required for simulating the model aspect of the observer. Combining the control system with neuromorphic hardware, for example in a system on chip, would significantly reduce the power consumption and provide a solution appropriate for portable realization. As emphasized in Schiff et al. (see Literature Reference No. 15), even if the results of closing the loop are a reduction in battery life the model-based paradigm would be beneficial. Ideally, extended battery life will be accompanied by clinical improvements and studies cited here support the presence of both in closed-loop strategies.

In addition to this, it has been suggested that the therapeutic restoration of the motor control is mechanistically dependent on the remodeling of the remaining spinal circuits (see, for example, Literature Reference No. 23). Having a control strategy as well as a model that are adaptive to the plastic changes within the spinal circuits requires less manual parameter adjustment over the life of the implant.

This invention may also prove efficacious in brain computer interfaces (BCI). Rather than contributing to the dynamic changes in brain dynamics, BCI applications would be used in estimating state and decoding measurements. Low-power realizations of these systems, as suggested here, offer a cost-effective option for BCI's.

The system and method according to various embodiments deals with two streams of physiological signals. First, stimulation is applied to a user via a device comprised of the electrode array 100 and battery pack and controller 102. The same stimulation data is simultaneously fed into a model of the spinal cord state as defined by function F (UKF/Kalman Observer). Motor output data are collected. The motor data can be collected in a number of ways (such as crudely through observation of desired/undesired motor behaviors or quantitatively (e.g., force plate sensors, electromyogram, motion capture)). Simultaneously, outputs are read out from function A, which are predicted motor responses tailored to be comparable to the same obtained physically. The UKF/Kalman Observer compares the outputs; should discrepancies arise, learning properties of the UKF modify the model and generate a new stimulation pattern based on this model to produce a desired output or goal state. Depending on therapies/treatment this goal state may differ. The UKF is agnostic to these requirements and may be adapted to a wide range of applications per the operator. Because the physical system 300 is dynamic and changing, it is advantageous to have a UKF system that constantly updates its models to better match the current state of the spinal cord anatomy. Additional information, such as (biological) sensory information, user input, and other sources of data can be used to granularize and improve the UKF.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for controlling epidural spinal cord stimulation, the system comprising:
   one or more processors and a memory, the memory being a non-transitory computer-readable medium having executable instructions encoded thereon, such that upon execution of the instructions, the one or more processors perform operations of:
   receiving sensed physiological signals from a subject and, based on the sensed physiological signals, estimating an unobservable state of a target area on the subject;
   generating a stimulation pattern based on the unobservable state for applying to the target area on the subject using an electrode array; and
   wherein the stimulation pattern is simultaneously applied to the target area of the subject and into a model of spinal cord state.

2. The system as set forth in claim 1, wherein the stimulation pattern is generated using a central pattern generator.

3. The system as set forth in claim 2, wherein in estimating the unobservable state of the target area of the subject, an Unscented Kalman Filter (UKF) is used that employs a set of known dynamical equations and observation functions with observable data to update an approximation of the unobservable state.

4. The system as set forth in claim 3, wherein the stimulation pattern is applied into the model of spinal cord state as defined by a Function F of the UKF.

5. The system as set forth in claim 4, wherein the UKF updates the model of the spinal cord based on predicted motor responses and the physiological signals, with the stimulation pattern modified based on the updates model of the spinal cord.

6. The system as set forth in claim 1, wherein in estimating the unobservable state of the target area of the subject, an Unscented Kalman Filter (UKF) is used that employs a set of known dynamical equations and observation functions with observable data to update an approximation of the unobservable state.

7. The system as set forth in claim 1, wherein the stimulation pattern is applied into the model of spinal cord state as defined by a Function F of an Unscented Kalman Filter (UKF).

8. The system as set forth in claim 7, wherein the UKF updates the model of the spinal cord based on predicted motor responses and the physiological signals, with the stimulation pattern modified based on the updates model of the spinal cord.

9. A method for controlling epidural spinal cord stimulation, the method comprising acts of:
   receiving sensed physiological signals from a subject and, based on the sensed physiological signals, estimating an unobservable state of a target area on the subject;
   generating a stimulation pattern based on the unobservable state for applying to the target area on the subject using an electrode array; and
   wherein the stimulation pattern is simultaneously applied to the target area of the subject and into a model of spinal cord state.

10. The method as set forth in claim 9, wherein the stimulation pattern is generated using a central pattern generator.

11. The method as set forth in claim 10, wherein in estimating the unobservable state of the target area of the subject, an Unscented Kalman Filter (UKF) is used that employs a set of known dynamical equations and observation functions with observable data to update an approximation of the unobservable state.

12. The method as set forth in claim 11, wherein the stimulation pattern is applied into the model of spinal cord state as defined by a Function F of the UKF.

13. The method as set forth in claim 12, wherein the UKF updates the model of the spinal cord based on predicted motor responses and the physiological signals, with the stimulation pattern modified based on the updates model of the spinal cord.

14. The method as set forth in claim 9, wherein in estimating the unobservable state of the target area of the subject, an Unscented Kalman Filter (UKF) is used that employs a set of known dynamical equations and observation functions with observable data to update an approximation of the unobservable state.

15. The method as set forth in claim 9, wherein the stimulation pattern is applied into the model of spinal cord state as defined by a Function F of an Unscented Kalman Filter (UKF).

16. The method as set forth in claim 15, wherein the UKF updates the model of the spinal cord based on predicted motor responses and the physiological signals, with the stimulation pattern modified based on the updates model of the spinal cord.

17. A computer program product for controlling epidural spinal cord stimulation, the computer program product comprising:
   a non-transitory computer-readable medium having executable instructions encoded thereon, such that upon execution of the instructions by one or more processors, the one or more processors perform operations of:
   receiving sensed physiological signals from a subject and, based on the sensed physiological signals, estimating an unobservable state of a target area on the subject;
   generating a stimulation pattern based on the unobservable state for applying to the target area on the subject using an electrode array; and
   wherein the stimulation pattern is simultaneously applied to the target area of the subject and into a model of spinal cord state.

18. The computer program product as set forth in claim 17, wherein the stimulation pattern is generated using a central pattern generator.

19. The computer program product as set forth in claim 18, wherein in estimating the unobservable state of the target area of the subject, an Unscented Kalman Filter (UKF) is used that employs a set of known dynamical equations and observation functions with observable data to update an approximation of the unobservable state.

20. The computer program product as set forth in claim 19, wherein the stimulation pattern is applied into the model of spinal cord state as defined by a Function F of the UKF.

21. The computer program product as set forth in claim 20, wherein the UKF updates the model of the spinal cord based on predicted motor responses and the physiological signals, with the stimulation pattern modified based on the updates model of the spinal cord.

22. The computer program product as set forth in claim 17, wherein in estimating the unobservable state of the target area of the subject, an Unscented Kalman Filter (UKF) is used that employs a set of known dynamical equations and observation functions with observable data to update an approximation of the unobservable state.

23. The computer program product as set forth in claim 17, wherein the stimulation pattern is applied into the model of spinal cord state as defined by a Function F of an Unscented Kalman Filter (UKF).

24. The computer program product as set forth in claim 23, wherein the UKF updates the model of the spinal cord based on predicted motor responses and the physiological signals, with the stimulation pattern modified based on the updates model of the spinal cord.

* * * * *